(12) United States Patent
Volkmuth et al.

(10) Patent No.: US 9,610,098 B2
(45) Date of Patent: Apr. 4, 2017

(54) LANCING DEVICE FOR TAKING BLOOD SAMPLES

(71) Applicant: Gerresheimer Regensburg GmbH, Regensburg (DE)

(72) Inventors: Julia Volkmuth, Maxhuette-Haidhof (DE); Andreas Eder, Regensburg (DE)

(73) Assignee: Gerresheimer Regensburg GMBH, Regensburg (DE)

( * ) Notice: Subject to any disclaimer, the term of this patent is extended or adjusted under 35 U.S.C. 154(b) by 361 days.

(21) Appl. No.: 14/046,503

(22) Filed: Oct. 4, 2013

(65) Prior Publication Data

US 2014/0155926 A1    Jun. 5, 2014

(30) Foreign Application Priority Data

Oct. 4, 2012   (DE) .................. 10 2012 019 401

(51) Int. Cl.
*A61B 17/34* (2006.01)
*A61B 5/15* (2006.01)
*A61B 5/151* (2006.01)

(52) U.S. Cl.
CPC ........ *A61B 17/3494* (2013.01); *A61B 5/1519* (2013.01); *A61B 5/150022* (2013.01); *A61B 5/15113* (2013.01); *A61B 5/15117* (2013.01); *A61B 5/150412* (2013.01);
(Continued)

(58) Field of Classification Search
CPC ............. A61B 17/3494; A61B 5/1519; A61B 5/15117; A61B 5/1411; A61B 5/15113; A61B 5/150022; A61B 5/150824; A61B 5/150412; A61B 5/150832; A61B 5/150259
See application file for complete search history.

(56) References Cited

U.S. PATENT DOCUMENTS

| 6,045,567 A | 4/2000 | Taylor et al. |
|---|---|---|
| 2006/0100656 A1 | 5/2006 | Olson et al. |

(Continued)

FOREIGN PATENT DOCUMENTS

| EP | 0 458 451 A1 | 11/1991 |
|---|---|---|
| EP | 1 649 814 A1 | 4/2006 |
| EP | 2 050 393 A1 | 4/2009 |

OTHER PUBLICATIONS

Examination Report issued on May 24, 2013, from the German Patent Office for German Patent Application No. 10 2012 019 400.5.
(Continued)

*Primary Examiner* — Corrine McDermott
*Assistant Examiner* — Tin Nguyen
(74) *Attorney, Agent, or Firm* — Lathrop & Gage LLP

(57) ABSTRACT

The invention relates to a lancing device (1) for taking blood samples, having a housing (2), an axially displaceable lancet holder element (32) for holding a lancet (12), a lancing spring element for accelerating the axially displaceable lancet holder element (32) in a lancing direction (18), and a release element (13) for initiating a lancing procedure, in which the axially displaceable lancet holder element (32) is accelerated in a lancing direction (18) by the tensioned lancing spring element, wherein the lancing device (1) comprises a locking apparatus (20), which can be released by the release element (13), for locking a lancing spring element tensioning procedure.

8 Claims, 3 Drawing Sheets

(52) U.S. Cl.
CPC .. *A61B 5/150824* (2013.01); *A61B 5/150832* (2013.01); *A61B 5/150259* (2013.01)

(56) References Cited

U.S. PATENT DOCUMENTS

| | | |
|---|---|---|
| 2008/0262388 A1* | 10/2008 | List ..................... A61B 5/1411 600/583 |
| 2009/0105613 A1 | 4/2009 | Nishiuchi |
| 2010/0094324 A1* | 4/2010 | Huang et al. ................. 606/182 |
| 2010/0160942 A1 | 6/2010 | Lamps et al. |
| 2012/0203259 A1 | 8/2012 | Saeki et al. |

OTHER PUBLICATIONS

Examination Report issued on May 28, 2013, from the German Patent Office for German Patent Application No. 10 2012 019 404.8.
Examination Report issued on May 27, 2013, from the German Patent Office for German Patent Application No. 10 2012 019 401.3.
European Search Report issued on Jan. 28, 2014, from the European Patent Office for European Patent Application No. 13186668.3.

* cited by examiner

LANCING DEVICE FOR TAKING BLOOD SAMPLES

CROSS REFERENCE TO RELATED APPLICATIONS

This application claims the benefit of and priority to German Application No. 10 2012 019 401.3, filed on Oct. 4, 2012, which is hereby incorporated by reference in its entirety.

DESCRIPTION

The invention relates to a lancing device for taking blood samples, comprising a housing, an axially displaceable lancet holder element for holding a lancet, a lancing spring element for accelerating the axially displaceable lancet holder element in a lancing direction, and a release element for initiating a lancing procedure, in which the axially displaceable lancet holder element is accelerated in a lancing direction by means of the tensioned lancing spring element.

Generic lancing devices are well known from the prior art. However, said hitherto known lancing devices are disadvantageous in that they can be accidentally released when the lancing spring is tensioned, that is to say when said lancing device is in an operating state ready for lancing. Here, the risk of unintentional injury to the user is relatively high.

The problem addressed by the present invention is to develop generic lancing devices to the extent that they are operationally safe for an inexperienced user to handle and operate, such that the risk of unintentional injury to the user is kept as low as possible.

The problem addressed by the invention is solved by a lancing device for taking blood samples, comprising a housing, an axially displaceable lancet holder element for holding a lancet, a lancing spring element for accelerating the axially displaceable lancet holder element in a lancing direction, and a release element for initiating a lancing procedure, in which the axially displaceable lancet holder element is accelerated in a lancing direction by means of the tensioned lancing spring element, wherein the lancing device comprises a locking apparatus, which can be released by the release element, for locking a lancing spring element tensioning procedure.

Owing to a mechanism of this type, it is made possible that the lancing device cannot be tensioned into an operating state ready for lancing or that the corresponding lancing spring element cannot be tensioned, should the release element have already been actuated or pushed by a user. As a result, unintended initiation of the lancing procedure is extremely easily prevented in a structural manner, such that the risk of unintentional injury to the user is also significantly reduced.

In particular, by means of the locking apparatus according to the invention, a displacement of a displaceably mounted tensioning carriage part for tensioning the lancing spring element is locked at least in part.

In this respect, a preferred variant provides that the release element is arranged in the housing of the lancing device such that a displacement of an axially slidably mounted tensioning carriage part of a tensioning unit of the lancing device into a front maximum sliding position is blocked by a radially directed actuating movement of the release element relative to the lancing direction.

A great advantage to this solution lies in general in that the lancing device cannot be tensioned if the release element is pushed just before tensioning or during tensioning of the lancing spring element.

Structurally, a locking apparatus of this type can be produced in a variety of ways. A very easy to construct and thus a favoured variant provides that the release element comprises at least a locking rib part for locking an axial tensioning movement of the axially slidably mounted tensioning carriage part in a lancing direction at least in part.

As a result, the present locking apparatus or at least parts thereof can be implemented in a particularly simple manner. This is advantageous in that the lancing device can be produced with a great reduction in components, despite an additional locking apparatus.

In addition, it is advantageous for the release element to comprise at least a locking rib part for locking an axial tensioning movement of the axially slidably mounted tensioning carriage element in a lancing direction at least in part. As a result, the locking apparatus can be provided in a structurally extremely simple manner at least in part.

If the at least one locking rib part extends from a push-piece and display head part of the release element into a longitudinal-extension sliding plane of an axially slidably mounted tensioning carriage part, in which the axially slidably mounted tensioning carriage part is arranged axially slidably at least in part, locking can be ensured in a very operationally safe manner.

The functionality can be further simplified if the longitudinal-extension sliding plane is arranged between the central longitudinal axis and the release element.

The functionality of the locking of the axially slidably mounted tensioning carriage part can be further improved if the at least one locking rib part comprises a locking bevel which is inclined in relation to the lancing direction.

In addition, if the at least one stop part comprises a stop bevel which faces a locking bevel of a locking rib part of the release element and is arranged opposite said locking bevel, advantageous locking can be achieved by this geometry.

In addition, it is advantageous for the locking apparatus to comprise at least one stop part, which is aligned with the lancing direction, for abutting the at least one locking rib part, the stop part being arranged on an axially slidably mounted tensioning carriage part. As a result, the axially slidably mounted tensioning carriage part can interact precisely with the at least one locking rib part.

An advantageous development of the present lancing device can be achieved if a display apparatus for displaying the respective operating states of the lancing device is provided, the display apparatus comprising the release element for initiating a lancing procedure in which the axially displaceable lancet holder element is accelerated in a lancing direction. Advantageously, when the lancing device is in an operating state ready for lancing, the release element is arranged in a disengaged display position projecting further outwards over the outer housing surface than when the lancing device is in a different operating state.

By means of the present release element, in particular a tensioning state of a lancing spring element of the lancing device can be displayed to a user in a structurally extremely simple manner; and this can take place indeed not only optically by the release element which projects further over the housing surface but advantageously also haptically, since this release element which projects further can be felt to be projecting by the user.

Advantageously, in this respect, additional functions are produced by components of the lancing device which are already present.

As a result, not only can a plurality of additional components, such as mechanics for controlling a colour display apparatus or the like, be omitted, but also the operational safety of the entire lancing device is further increased by the option of feeling the operating state. This is greatly advantageous in particular for users with visual impairments.

This is particularly advantageous in recyclable lancing devices comprising replaceable lancets, since the user repeatedly tensions said lancing devices manually so as to be ready for lancing.

The lancing direction is preferably aligned here with the longitudinal axis in the longitudinal extension of the lancing device, whereby the construction can be kept structurally simple.

A further advantageous variant provides that, in the case of a tensioned lancing spring element, the release element is arranged so as to project radially further outwards over the outer housing surface in relation to the lancing direction than in the case of an untensioned lancing spring element. As a result, very advantageous and thus good single-handed operation can be achieved.

Another preferred variant also provides that the release element is arranged in the housing of the lancing device such that it can be disengaged from the housing by an axially slidably mounted tensioning carriage part of a tensioning unit of the lancing device.

The release element is, in general, ideally mounted in translation in certain guide grooves and/or webs formed by the housing and preferably radially slidably in relation to the axial lancing direction.

The release element can be moved into the disengaged display position in a structurally simple manner within the meaning of the invention if the release element comprises a disengagement rib part for introducing disengagement forces into the release element.

Ideally, said disengagement rib part also comprises the locking rib part, such that the present construction can again be significantly simplified.

The disengagement rib part is preferably formed identically to said locking rib part, such that features relating to the disengagement rib part can also apply to the present locking rib part.

The lancing device can be constructed in a more compact manner with respect to the above functions if the disengagement rib part also extends from a push-piece and display head part of the release element into a longitudinal-extension sliding plane of an axially slidably mounted tensioning carriage part, in which the axially slidably mounted tensioning carriage part is arranged axially slidably at least in part.

This functionality can also be further simplified if the longitudinal-extension sliding plane is arranged between the central longitudinal axis and the release element.

The operational safety of the lancing device can be further increased if the disengagement rib part comprises a disengagement bevel which is inclined in relation to the lancing direction.

If this inclined disengagement bevel is facing the axially slidably mounted tensioning slide carriage part, the risk of a tensioning procedure requiring excessive sliding forces can be reduced.

Ideally, two disengagement ribs are provided such that in the direction transverse to the lancing direction, there are two mutually spaced disengagement bevels which are inclined in relation to the lancing direction, whereby the risk of the release element tilting for example in the guide grooves and/or webs of the housing or the like can be significantly reduced.

For advantageously and safely tensioning in particular a lancing spring element of a drive unit for accelerating the axially displaceable lancet holder element of the lancing device, said device ideally comprises a tensioning unit comprising a manually actuatable tensioning slide element.

It will be understood that the drive unit can also be configured in a variety of ways. It advantageously comprises at least two spring elements, including the lancing spring element for accelerating the axially displaceable lancet holder element in the lancing direction and a return spring element for accelerating the axially displaceable lancet holder element counter to the lancing direction. In particular as a result, overshooting of the spring elements is advantageously not necessary, since a forward movement during the lancing procedure and the subsequent return movement after the actual lancing procedure are performed by two separate spring elements. The spring elements used in this case preferably comprise helical spring elements.

In the present case, at least the axially displaceable lancet holder element thus moves in translation in the lancing direction in order to perform a lancing procedure. It moves in translation counter to this lancing direction in order to displace the lancet back into the housing.

By means of said above-mentioned tensioning slide element, at least the axially slidably mounted tensioning carriage part can be moved in translation to tension the lancing spring element in the lancing direction.

In this respect, with regard to a structurally yet more simply constructed and very easy to use lancing device, it is advantageous for the tensioning unit to be provided with at least the axially slidably mounted tensioning carriage part, the axially slidably mounted tensioning carriage part comprising at least an actuation element for disengaging the release element.

It will be understood that said actuation element can be configured in a variety of ways. The at least one actuation element advantageously comprises an arm part aligned in the lancing direction, which arm part comprises an actuation bevel which is inclined in relation to the lancing direction in order to be able to interact with the disengagement rib part when tensioning the lancing spring element such that the release element is only moved into the disengaged display position with low force expenditure.

In this case, it is advantageous for the inclined actuation bevel to face in particular the inclined disengagement bevel, since an interaction between the axially slidably mounted tensioning slide carriage part and the release element can be significantly improved thereby.

If the release element is distinguished by two disengagement ribs, it is advantageous for the actuation part to alternatively comprise two such aligned arm elements which are arranged in the lancing direction and with spacing transverse thereto.

Owing to the above-described measures, it is achieved both in a structurally and a functionally very simple manner that by a simple tensioning procedure of the lancing spring element with respect to translatory sliding of the tensioning slide element towards the longitudinal axis of the lancing device, the release element is disengaged radially in relation to the longitudinal axis into the disengaged display position.

In order for it to be possible to also hold the release element in said disengaged display position when the tensioning slide element has already been displaced back by spring force, the present lancing device is furthermore advantageously distinguished by a holding apparatus for temporarily holding the release element in said disengaged display position.

It will be understood that said holding apparatus can also be constructed in a variety of ways.

The holding apparatus preferably comprises snap elements on the release element and corresponding elevation elements on the housing, behind which elevation elements said snap elements can snap.

As a result, it can be ensured that the release element is securely snapped into the disengaged display position. In addition, as a result it can also be ensured in a structurally simple manner that until the release element is manually pressed, it remains securely in the disengaged display position.

Should the tensioning unit also comprise a tensioning carriage part which can be axially fixed in a tensioning position for holding the lancing spring element in a tensioned state, it is advantageous for the fixable tensioning carriage part to be temporarily axially fixed in this tensioning position by means of a latching apparatus which can be latched to the axially displaceable lancet holder element, since the structural complexity can be further reduced thereby and the handling of the lancing device can be further simplified.

Another structural advantage is that the fixable tensioning carriage part can be mounted in the housing at least in part such that it can also move along the displacement axis in order that it can be displaced into or out of the tensioning position.

In this respect, this lancing direction also forms the displacement axis along which or in the direction of which in particular the axially displaceable lancet holder element moves in translation inside the housing.

The axially displaceable lancet holder element thus ideally forms in a structurally simple manner a lancing carriage part inside the housing of the present lancing device.

An advantageous variant provides that a latching apparatus comprises, for axially fixing the fixable tensioning carriage part, a latching arm element which can be deflected radially in relation to the lancing direction and which interacts with the axially displaceable lancet holder element during fixing of the fixable tensioning carriage part in the tensioning position. As a result, the latchable latching apparatus can be implemented in a structurally particularly simple manner.

A deflectable latching arm element of this type can be bent in a structurally simple, ideally elastic manner.

The elastically deflectable latching arm element is preferably elastically bendable at least in two different paths. In this case, the two different paths preferably extend at right angles to each other.

In this respect, the elastically deflectable latching arm element is repeatedly bendable.

The lancing device is thus ideally distinguished by a tensioning apparatus comprising a tensioning carriage part which can be fixed in a tensioning position in which the lancing spring element is tensioned, in which the fixable tensioning carriage part can be temporarily fixed in the tensioning position by means of the latching apparatus of the lancing device, the latching apparatus comprising a latching arm element which can be latched by means of the lancet holder element, by means of which arm element the latchable tensioning carriage part is arranged so as to be temporarily axially fixed in the tensioning position as long as the latchable latching arm element is fixed to said lancet holder element.

A further preferred variant further provides that the latching apparatus is arranged in the housing such that a latching arm element which can be deflected radially in relation to the lancing direction is arranged such that it can be disengaged radially by a translatory change in position of the axially displaceable lancet holder element in the lancing direction, such that the fixable tensioning carriage part can be displaced in translation from the tensioning position into a relaxed position with the help of a compression spring element. As a result, it is possible in a structurally simple manner to return the fixable tensioning carriage part to its original resting position or release position in order to reliably prepare the lancing device for a new lancing procedure, for example for a safe change of lancet.

It is also advantageous for the latching apparatus to interact with the fixable tensioning carriage part on the basis of a relative axial position of the axially displaceable lancet holder element in relation to the housing. A very simple design of the mechanics can be achieved as a result.

A further structural simplification can be achieved when the latching apparatus comprises a sleeve part which radially surrounds the axially displaceable lancet holder element externally at least in part.

Structurally simple interaction between the latchable latching apparatus and the axially displaceable lancet holder element can be achieved when the axially displaceable lancet holder element comprises a latching rib which can be engaged from behind by the latchable latching apparatus and which is arranged so as to extend axially at least in part on the displaceable lancet holder element.

The latching rib which can be engaged from behind is ideally positioned on the axially displaceable lancet holder element such that said rib is out of reach of the deflectable latching arm element of the latchable latching apparatus when the axially displaceable lancet holder element is in or not far short of its lancing end position.

Another advantageous variant provides that the latching apparatus which can be latched to the axially displaceable lancet holder element comprises means for fixing the fixable tensioning carriage part. This is particularly advantageous when the latchable latching apparatus is not directly assigned to the fixable tensioning carriage.

In this connection, the means for fixing the fixable tensioning carriage part can be in a variety of forms. For example, they include tongue elements or groove elements of a tongue and groove joint, which can interact with the corresponding counter elements on the fixable tensioning carriage part when this is in the tensioning position.

In particular, operation of the lancing device can also be made significantly easier when the tensioning unit comprises a further tensioning carriage part for displacing the fixable tensioning carriage part, the further tensioning carriage part comprising a shaped element for radial engagement of the latching apparatus which can be latched to the axially displaceable lancet holder element.

This further tensioning carriage part comprises the axially slidably mounted tensioning carriage part.

This further tensioning carriage part can advantageously be slid manually along the displacement axis in the lancing direction by means of the tensioning slide element which is accessible outside the housing, such that the fixable tensioning carriage part can be displaced into the tensioning position manually and in a structurally simple manner.

The shaped element assigned to the further tensioning carriage part can also have a variety of structural forms. With regard to a preferred design variant, it is advantageous for said shaped element to comprise a sliding guide face which is inclined in relation to the lancing direction. As a result it is possible in a structurally very compact manner to switch a movement of the further tensioning carriage part directed axially along the displacement axis into a movement of the latchable latching apparatus or the deflectable latching arm element directed radially in relation to the displacement axis.

The present lancing device can generally be constructed in an even more compact manner, and thus again in a manner which is easier to handle, when the axially displaceable lancet holder element, the fixable tensioning carriage part or the further tensioning carriage part of the tensioning apparatus each comprise a sleeve part.

In this connection, it is particularly advantageous for individual ones of the sleeve parts to be arranged in the housing such that they can be slid along the displacement axis, for example in a telescoped manner.

In this respect, it is extremely advantageous for the axially displaceable lancet holder element, the fixable tensioning carriage part and/or the further tensioning carriage part to have a common displacement axis.

The displacement axis preferably coincides with the central longitudinal axis.

It is also particularly advantageous for the present kinematics of the drive unit in terms of the tensioning procedure and the actual lancing procedure to be implemented substantially by the two tensioning carriage parts of the tensioning unit and by the lancing carriage part, which are arranged such that they can be telescoped at least in part.

A further structural simplification of the lancing device can be achieved when the lancing device comprises a two-part housing comprising an upper shell part and a lower shell part on which at least the axially slidably mounted tensioning carriage part is guided directly in translation.

In any case, the release element and the axially slidably mounted tensioning carriage part are arranged in the housing of the lancing device such that either a tensioning procedure of the lancing spring element can be locked or a lancing procedure can be initiated by means of an actuated release element on the basis of an axial position of the axially slidably mounted tensioning carriage part.

Further advantages, aims and properties of the present invention will be described by way of the appended drawings and the following description, in which by way of example a lancing device according to the invention for taking blood samples is shown and described.

IN THE DRAWINGS

Figure 1:
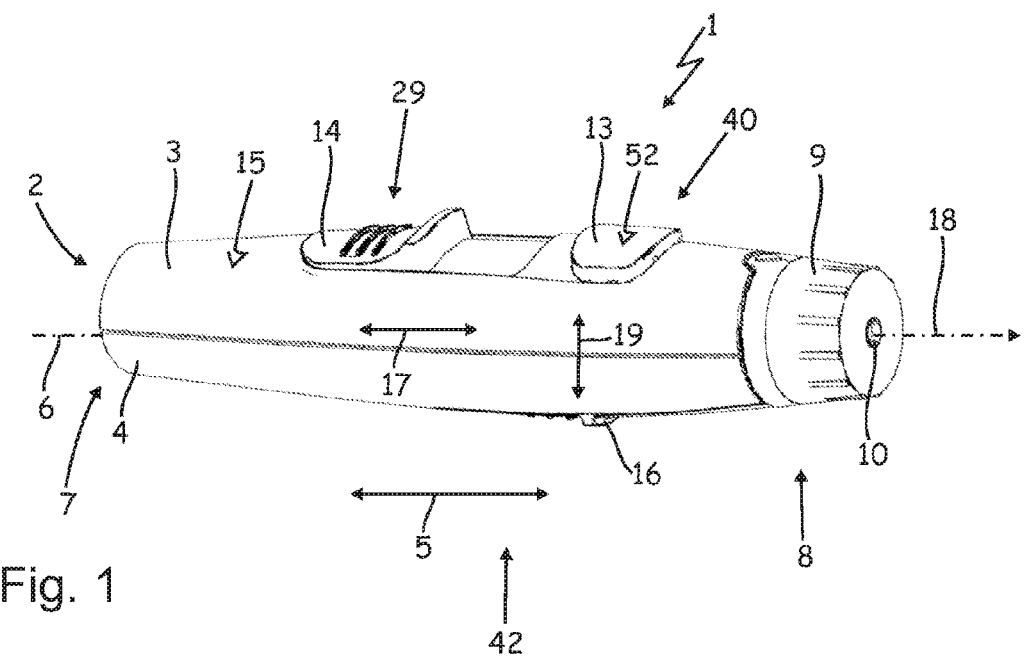
FIG. 1 shows schematically an overview of a lancing device for taking blood samples comprising a locking apparatus according to the invention.

The lancing device 1 shown in FIGS. 1 to 7 is intended for taking a blood sample. The lancing device 1 comprises a two-part housing 2 comprising an upper shell part 3 and a lower shell part 4.

The lancing device 1 extends with a longitudinal extension 5 along a longitudinal axis 6 from an end region 7 of the lancing device 1 to a head region 8 of the lancing device 1, a screw cap 9 having a feed-through opening 10 for a lancing needle 11 of a replaceable lancet 12 (see for example FIG. 2) of the lancing device 1 being screwed into the two-part housing 2 in this head region 8 of the lancing device 1. In this embodiment, the longitudinal axis 6 is also the central longitudinal axis of the lancing device 1.

On the upper shell part 3, a release pressure element 13 for initiating a lancing procedure using the lancing device 1 and a tensioning slide element 14, which both project radially beyond the outer face 15 of the two-part housing 2 such that they are easily manually accessible, are located radially adjacent to the longitudinal axis 6.

On the lower shell part 4, an ejector slide element 16, which likewise projects radially beyond the outer housing surface 15 of the two-part housing 2 so as also to be manually accessible without difficulty, is located radially adjacent to the longitudinal axis 6.

While the tensioning slide element 14 and the ejector slide element 16 are displaceable axially along the longitudinal axis 6 in axial directions 17 and in particular in the lancing direction 18, the release pressure element 13 is displaceable radially in relation to the longitudinal axis 6 in radial directions 19.

Figure 2:
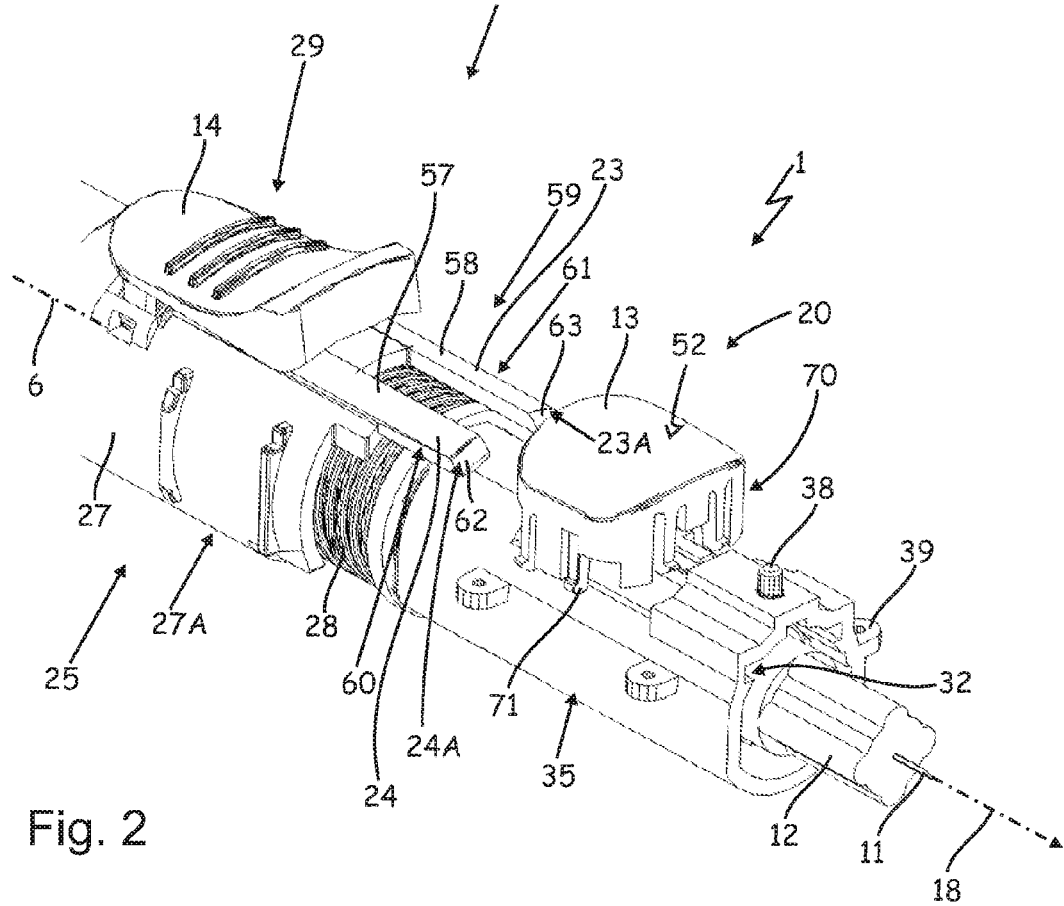
FIG. 2 shows schematically a perspective model view of the lancing device from FIG. 1, but without the housing.

The illustration according to FIG. 2 shows the lancing device 1 without the housing 2.

The lancing device 1 is distinguished by a locking apparatus 20 which can be released by the release element 13 for locking a lancing spring element tensioning procedure.

Figure 6:
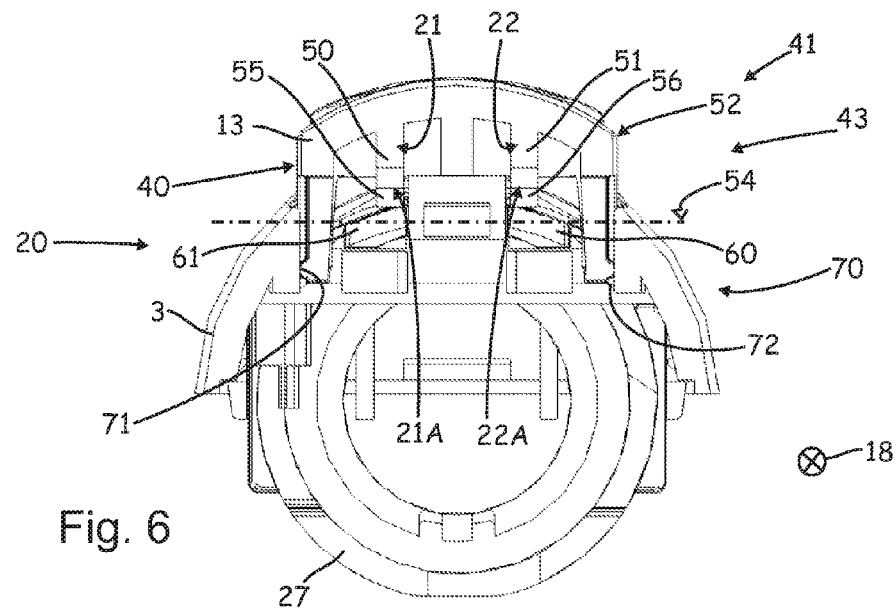
FIG. 6 shows schematically a rear cross-sectional view of the lancing device from FIGS. 1 to 5 at the level of the radially disengaged release element.

The locking apparatus 20 is distinguished on one hand by locking rib parts 21 and 22 provided on the release element 13, which provide inclined locking bevels 21A and 22A in relation to the lancing direction 18 (see FIG. 6).

On the other hand, the locking apparatus 20 also comprises two stop parts 23 and 24 aligned with the lancing direction 18 (see FIG. 2) for abutting the locking rib parts 21 and 22, whereby the tensioning procedure of the lancing device 1 can be locked in a structurally simple manner if the release element 13 is pushed accidentally or deliberately.

The locking bevels 21A and 22A can advantageously interact with the stop bevels 23A and 24A when locking the tensioning procedure, since the locking bevels 21A, 22A face the stop bevels 23A and 24A and are arranged opposite said stop bevels.

The tensioning slide element 14 is a component of a tensioning unit 25 of the lancing device 1, the tensioning unit 25 further comprising at least an axially slidably mounted tensioning carriage part 27 for axially displacing a fixable tensioning carriage part (not shown here) and a tensioning carriage spring element 28 for displacing the axially slidably mounted tensioning carriage part 27 and the tensioning slide element 14 back into a rear starting position 29 after a tensioning procedure.

The fixable tensioning carriage part and the axially slidably mounted tensioning carriage part 27 are not fixed rigidly to one another but are mounted such that they can be slid axially in relation to one another; however, the fixable tensioning carriage part is entrained by the axially slidably mounted tensioning carriage part 27 when the axially slidably mounted tensioning carriage part 27 is manually displaced in the lancing direction 18 by means of the tensioning slide element 14.

In this connection, both the fixable tensioning carriage part and the axially slidably mounted tensioning carriage part 27 are designed as sleeve parts 27A, the sleeve part (not shown here) of the fixable tensioning carriage part being mounted such that it can be slid axially inside the further tensioning carriage part 27, at least in part, and the sleeve part 27A of the axially slidably mounted tensioning carriage part 27 being mounted such that it can be slid axially in the upper and lower shell parts 3 and 4 of the two-part housing 2.

The axially slidably mounted tensioning carriage part 27 is connected with a positive fit to the tensioning slide element 14 (see in particular FIG. 2), whereby said tensioning carriage part can be actuated manually by means of the tensioning slide element 14 without difficulty.

If said tensioning slide element 14 is slid in the lancing direction 18 by the axially slidably mounted tensioning carriage part 27 while the release element 13 is being pushed, the stop bevels 23A and 24A of the stop arms 23 and 24 arranged on the axially slidably mounted tensioning carriage part 27 come into contact with the locking bevels 21A, 22A of the locking rib elements 21 and 22 provided on the release element 13, whereby further displacement in particular of the axially slidably mounted tensioning carriage part 27 into a front maximum sliding position 73 (see FIGS. 4 and 5) is no longer possible. The lancing spring element cannot be tensioned.

The lancing device 1 also comprises a latching apparatus (not shown here) which as a sleeve part 35 in the two-part housing 2 is rigidly fixed to the upper and lower shell parts 3 and 4 and is thus axially secured against sliding.

Advantageously, the sleeve part 35 simultaneously also serves as a mounting and guiding apparatus for axial and radial mounting of an axially displaceable lancet holder element 32, whereby the lancing device 1 again has a reduced number of components and thus a more compact design.

In order that the sleeve part 35 can be mounted in particular in a twist-proof manner in the housing 2 of the lancing device 1, the sleeve part 35 comprises some stay bolts 38 (given a reference numeral only by way of example) and screw tabs 39 (also given a reference numeral only by way of example), by means of which the sleeve part 35 can be fastened to the housing 2 in a stationary manner.

The release element 13 also forms a display apparatus 40 for displaying the respective operating states 41 or 42 of the lancing device 1.

If the lancing device 1 is in an operating state 41 ready for lancing (see FIGS. 4, 5 and 6), the release element 13 projects further outwards over the outer housing surface 15 of the lancing device 1 in a disengaged display position 43 than in different operating states 42 (see FIGS. 1, 2, 3 and 7), in which the lancing device 1 is not yet ready for lancing or is no longer ready for lancing.

In all the operating states 42 which are different from the operating state 41 ready for lancing, the release element 13 is not in the disengaged display position 43.

As a result, the operating state 41 ready for lancing is advantageously signalled and indicated or produced optically, haptically and structurally in an extremely simple manner.

In this respect, the release element 13 is arranged in the housing 2 such that it can be disengaged radially from the housing 2 by the axially slidably mounted tensioning carriage part 27.

It will be understood that this functionality can be implemented in a variety of ways.

In the present embodiment, the release element 13 has two disengagement rib parts 50 and 51 (see in particular FIG. 6) for introducing disengagement forces into the release element 13 and thus also for radially disengaging the release element 13 from the housing 2 of the lancing device 1 into the disengaged display position 43.

In this embodiment, the two disengagement rib parts 50 and 51 are in particular structurally identical to the locking rib parts 21 and 22.

These two disengagement rib parts 50, 51 each extend in this respect from a push-piece and display head part 52 of the release element 13 radially downwards 53 (see FIG. 4) towards the longitudinal axis 6 of the lancing device 1, such that these are arranged on the release element 13 so as to be easily axially accessible by the axially slidably mounted tensioning carriage part 27.

In particular, the two disengagement rib parts 50, 51 pass through a longitudinal-extension sliding plane 54 (see FIG. 3) of the axially slidably mounted tensioning carriage part 27 when the release element 13 is not yet in the disengaged display position 43.

Said longitudinal-extension sliding plane 54 is positioned between the central longitudinal axis of the lancing device 1 and the release element 13 or the push-piece and display head part 52.

In order to be able to interact in particular without tilting with the axially slidably mounted tensioning carriage part 27, the two disengagement rib parts 50 and 51 each comprise a disengagement bevel 55 and 56 which is inclined in relation to the lancing direction 18, which bevels are accordingly also arranged so as to be inclined in relation to the longitudinal-extension sliding plane 54.

Interaction between the axially slidably mounted tensioning carriage part 27 and the release element 13 is further improved since the axially slidably mounted tensioning carriage part 27 is provided with two actuation elements 57 and 58 for disengaging the release element 13.

Said actuation elements 57, 58 extend, when viewed in the lancing direction 18, on the head side 59 of the axially slidably mounted tensioning carriage part 27 in the form of two arm parts 60 and 61 extending mutually parallel.

Said arm parts 60 and 61 in turn each provide actuation bevels 62 and 63 (see FIG. 2) which are inclined in relation to the lancing direction 18, which bevels interact with the inclined disengagement bevels 55 and 56 as counter-faces when the axially slidably mounted tensioning carriage part 27 is moved axially in the lancing direction 18, and in this case the release element 13 is moved radially into the disengaged display position 43.

The lancing device 1 has a holding apparatus 70 for temporarily holding the release element 13 in the disengaged display position 43.

In this embodiment, the holding apparatus 70 is formed such that it comprises a plurality of snap elements 71 (given a reference numeral here only by way of example) on the release element 13 and a plurality of elevation elements 72 (given a reference numeral only by way of example) on the housing 2, behind which elevation elements said snap elements 71 can snap (see in particular FIG. 6).

Figure 3:
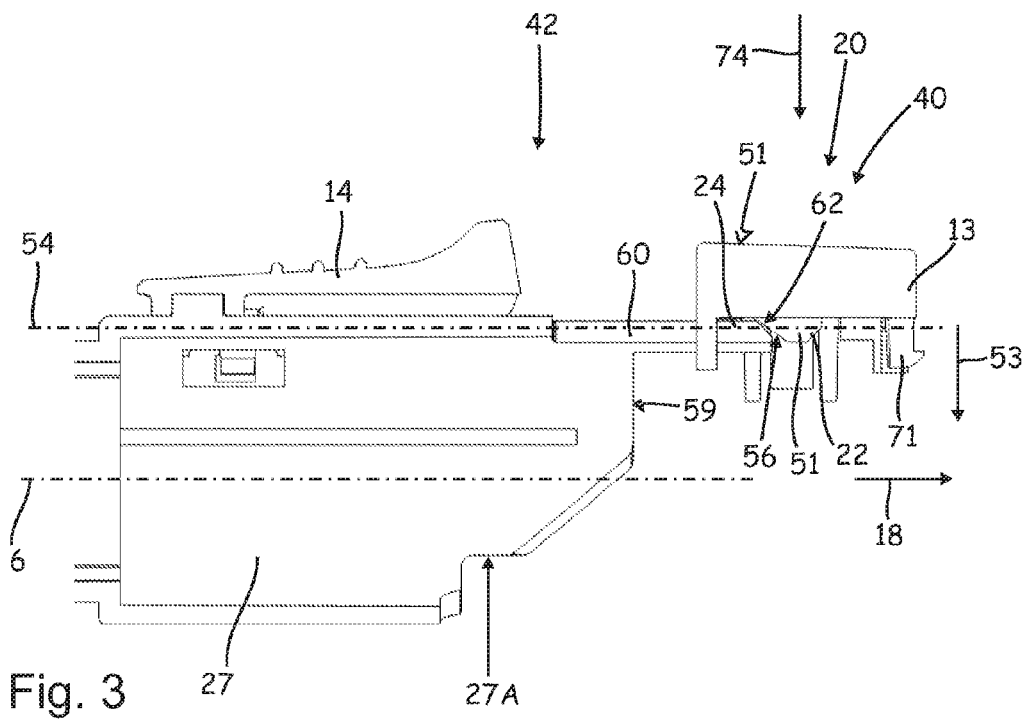
FIG. 3 shows schematically a first functional side view of the lancing device from FIGS. 1 and 2 comprising an active locking apparatus, in which stop parts of an axially slidably mounted tensioning carriage part rest axially against locking rib parts of the release element in relation to the lancing direction.

While in particular the axially slidably mounted tensioning carriage part 27 of the lancing device 1 is still in the rear starting position 29 with respect to the illustrations according to FIGS. 1 and 2, this axially slidably mounted tensioning carriage part 27 in the illustration according to FIG. 3 is already axially manually slid forward in the lancing direction 18 such that the inclined actuation bevels 62 and 63 thereof rest on the inclined disengagement bevels 55 and 56 of the release element 13. In this case, the release element 13 is not yet radially disengaged.

If a user now intentionally or unintentionally exerts a manual actuation force 74 on the release element 13, the axially slidably mounted tensioning carriage part 27 is blocked in the lancing direction 18. In this respect, the locking apparatus 20 is produced in a structurally simple manner without additional components. Additional operation of the locking apparatus 20 is also unnecessary.

Figure 4:
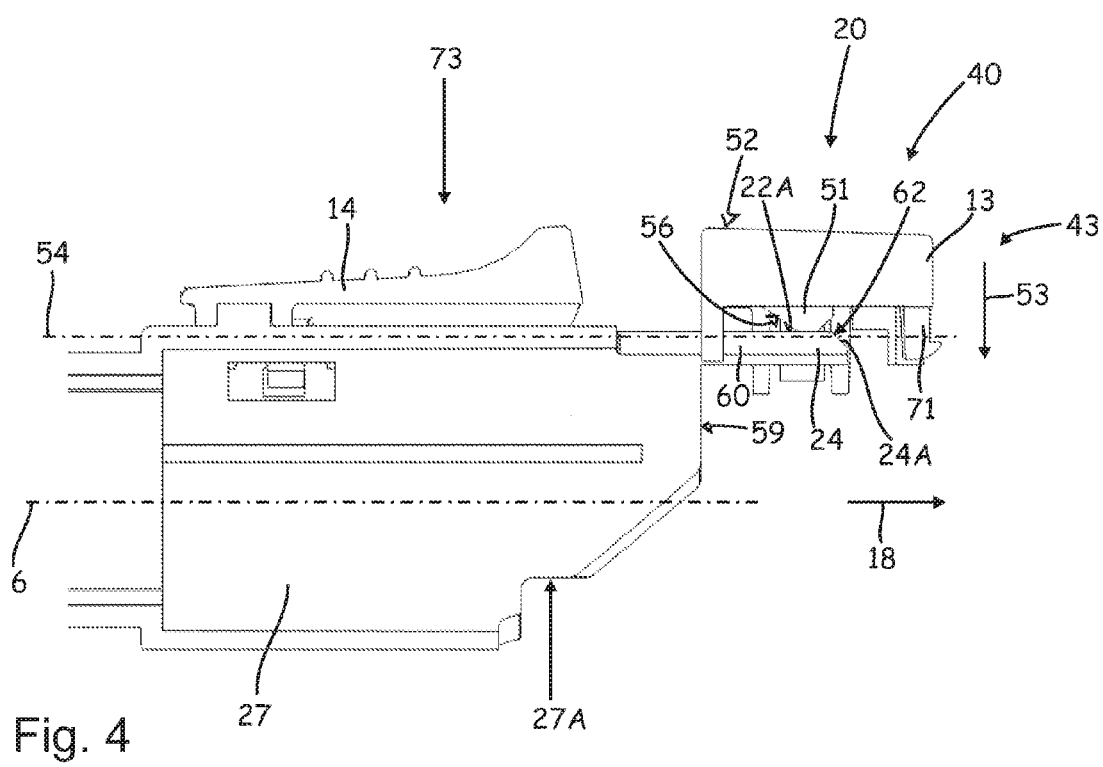
FIG. 4 shows schematically a further functional side view of the lancing device from FIGS. 1 to 3, in which the stop parts are arranged radially under the locking rib parts of the release element in relation to the lancing direction.
Figure 5:
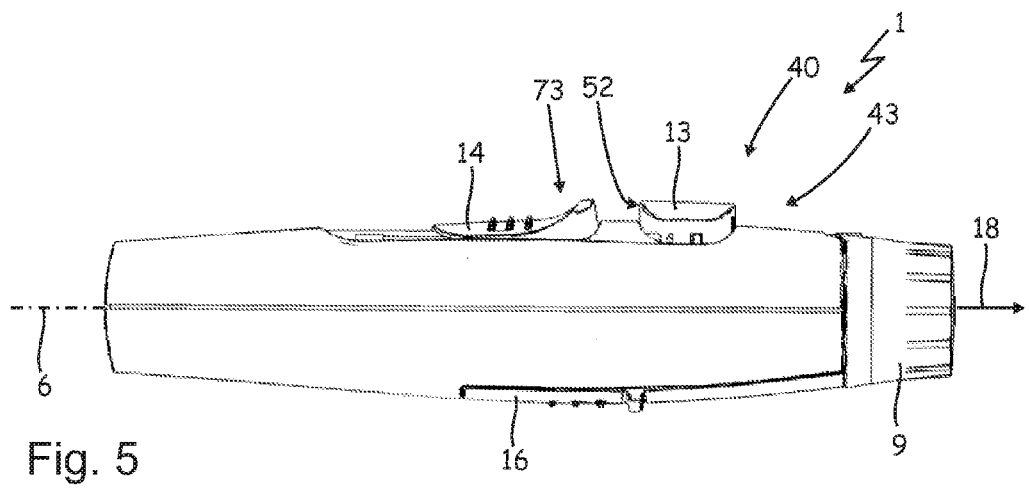
FIG. 5 shows schematically a further overview of the lancing device from FIGS. 1 to 4 according to the operating state shown in FIG. 4.

However, if the release element 13 is not pushed, the axially slidably mounted tensioning carriage part 27 can be slid further in the lancing direction 18, as shown in FIGS. 4 and 5.

The illustrations according to FIGS. 4 and 5 show the axially slidably mounted tensioning carriage part 27 now in a maximum sliding position 73 which is displaced maximally in the lancing direction 18, in which position the release element 13 is already in the disengaged display position 43. In this front maximum sliding position 73, the two arm parts 60 and 61 of the actuation elements 57 and 58 completely engage under the two disengagement rib parts 50 and 51 of the release element 13 and lift said element with the snap elements 71 of the holding apparatus 70 over the elevation elements 72 of the holding apparatus 70, whereby the release element 13 also remains in the disengaged display position 43 when the axially slidably mounted tensioning carriage part 27 then springs back or is sprung back again into the rear starting position 29 counter to the lancing direction 18 with the help of spring forces (see FIG. 6).

Figure 7:
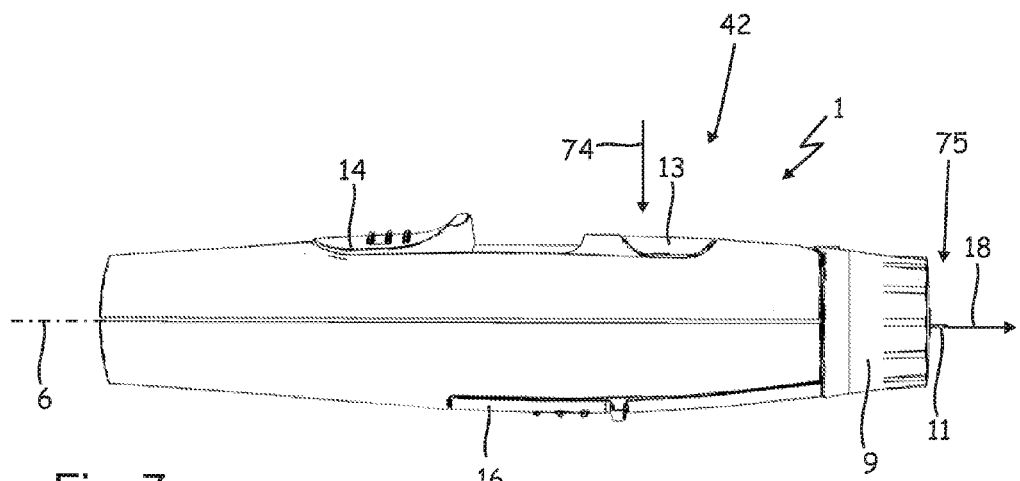
FIG. 7 shows schematically another overview of the lancing device from FIGS. 1 to 6 in a released lancing state.

The illustration according to FIG. 7 shows the lancing device 1 already in a released state, in which the release element 13 is pushed radially into the housing 2 by a manual actuation force 74 and by overcoming the holding forces applied by the holding apparatus 70 and the lancing needle 11 of the lancet 12 is already arranged in the lancing end position 75.

The tensioning mechanism described above can also be used when the tensioning slide element 14 is alternatively positioned at the end region 7 as a push button (not shown here) or the like.

In the present case, the release element 13 advantageously takes on two further functions in addition to the actual release function, namely that of a locking apparatus 20 and that of a display apparatus 40.

In this respect, it is extremely advantageous for the locking apparatus 20 and the display apparatus 40 to be structurally identical or at least to be formed structurally identically with respect to their essential components, such that the lancing device 1 is constructed in a structurally simple manner despite these functions, and in addition is easy for even an inexperienced user to handle.

It will be understood that the embodiment described above is merely a first configuration of the lancing device according to the invention. In this respect, the configuration of the invention is not limited to this one embodiment.

Certain features disclosed in the application are understood to be novel, including for example features either individually or in combination with other features as compared with the prior art.

LIST OF REFERENCE NUMERALS 1 lancing device
2 two-part housing
3 upper shell part
4 lower shell part
5 longitudinal extension
6 longitudinal axis
7 end region
8 head region
9 screw cap
10 feed-through opening
11 lancing needle
12 lancet
13 release pressure element
14 tensioning slide element
15 outer housing surface
16 ejector slide element
17 axial directions
18 lancing direction
19 radial directions
20 locking apparatus
21 left locking rib part
21A left locking bevel
22 right locking rib part
22A right locking bevel
23 left stop part
23A left stop bevel
24 right stop part
24A right stop bevel
25 tensioning unit
27 axially slidably mounted tensioning carriage part
27A sleeve part of the tensioning carriage part
28 tensioning carriage spring element
29 rear starting position
32 axially displaceable lancet holder element
35 sleeve part of a latching apparatus
38 stay bolts
39 screw-receiving tabs
40 display apparatus
41 operating state ready for lancing
42 operating states not ready for lancing
43 disengaged display position
50 left disengagement rib part
51 right disengagement rib part
52 push-piece and display head part
53 downwards
54 longitudinal-extension sliding plane
55 inclined left disengagement bevel
56 inclined right disengagement bevel
57 right actuation element
58 left actuation element
59 head side
60 right arm part
61 left arm part
62 inclined right actuation bevel
63 inclined left actuation bevel
70 holding apparatus
71 snap elements
72 elevation elements
73 front maximum sliding position
74 manual actuation force
75 lancing end position

We claim:

1. A lancing device for taking blood samples, comprising a housing, an axially displaceable lancet holder element for holding a lancet, a lancing spring element for accelerating the axially displaceable lancet holder element in a lancing direction, and a release element for initiating a lancing procedure, in which the axially displaceable lancet holder element is accelerated in the lancing direction by means of the tensioned lancing spring element, wherein said lancing spring element is initially tensioned in a tensioning procedure by displacement of an axially slidably mounted tensioning carriage part, wherein the lancing device comprises a locking apparatus for locking said lancing spring element in the tensioning procedure, wherein the locking is actuated by the release element, and wherein the locking apparatus comprises at least one stop part for abutment with at least one locking rib part of the release element, the at least one stop part being arranged on said tensioning carriage part, wherein by said abutment the displacement in the lancing direction of said tensioning carriage part is prevented; wherein a locking movement of the release element moves the at least one locking rib part into abutment with the at least one stop part.

2. The lancing device according to claim 1, wherein the release element is arranged in the housing of the lancing device such that said displacement of the axially slidably mounted tensioning carriage part of a tensioning unit of the lancing device into a front maximum sliding position is blocked by a radially directed actuating movement of the release element in relation to the lancing direction.

3. The lancing device according to claim 1, wherein the at least one locking rib part extends from a push-piece and display head part of the release element into a longitudinal-extension sliding plane of the axially slidably mounted tensioning carriage part, in which the axially slidably mounted tensioning carriage part is arranged axially slidably at least in part.

4. The lancing device according to claim 3, wherein the longitudinal-extension sliding plane is arranged between a central longitudinal axis and the release element.

5. The lancing device according to claim 1, wherein the at least one locking rib part comprises a locking bevel which is inclined in relation to the lancing direction.

6. The lancing device according to claim 5, wherein the at least one stop part comprises a stop bevel which faces a locking bevel of the at least one locking rib part of the release element and is arranged opposite said locking bevel.

7. The lancing device according to claim 1, wherein the at least one stop part is aligned with the lancing direction.

8. The lancing device according to claim 1, wherein at least the axially slidably mounted tensioning carriage part can be moved in translation to tension the lancing spring element in the lancing direction.

* * * * *